United States Patent [19]

Crutzen

[11] Patent Number: 4,842,758
[45] Date of Patent: * Jun. 27, 1989

[54] STABILIZED ENZYME SYSTEM FOR USE IN AQUEOUS LIQUID BUILT DETERGENT COMPOSITIONS

[75] Inventor: Andre Crutzen, Sclessin, Belgium

[73] Assignee: Colgate-Palmolive Company, New York, N.Y.

[*] Notice: The portion of the term of this patent subsequent to Jun. 27, 2006 has been disclaimed.

[21] Appl. No.: 925,437

[22] Filed: Oct. 31, 1986

[51] Int. Cl.$^4$ .................. C11D 3/33; C11D 3/386; D06M 11/00

[52] U.S. Cl. .................... 252/8.7; 252/8.6; 252/891; 252/135; 252/156; 252/525; 252/532; 252/534; 252/539; 252/DIG. 12; 433/188

[58] Field of Search ............ 252/174.12, DIG. 12, 252/135, 156, 89.1, 539, 525, 8.6, 8.7, 532, 534; 433/188

[56] References Cited

U.S. PATENT DOCUMENTS

| 3,296,094 | 1/1967 | Cayle | 195/63 |
| 3,325,364 | 6/1967 | Merritt et al. | 167/73 |
| 3,558,498 | 1/1971 | Eymery et al. | 252/135 |
| 3,560,392 | 2/1971 | Eymery et al. | 252/138 |
| 4,115,292 | 9/1978 | Richardson et al. | 252/90 |
| 4,238,345 | 12/1980 | Guilbert | 252/174.12 |
| 4,404,115 | 9/1983 | Tai | 252/135 |
| 4,469,605 | 9/1984 | Ramachandran et al. | 252/8.7 |
| 4,529,525 | 7/1985 | Dormal et al. | 252/108 |
| 4,532,064 | 7/1985 | Boskamp | 252/105 |
| 4,537,707 | 8/1985 | Severson, Jr. | 252/545 |

FOREIGN PATENT DOCUMENTS

| 080223 | 6/1983 | European Pat. Off. | 252/174.12 |
| 2079305 | 6/1981 | United Kingdom . | |
| 2140819 | 12/1984 | United Kingdom | 252/174.12 |

OTHER PUBLICATIONS

Freeman, A. "Understanding Enzyme Stabilization" *Trends in Biotechnology*, vol. 2, No. 6, 1984, pp. 147–148.

Primary Examiner—A. Lionel Clingman
Assistant Examiner—Linda D. Skaling
Attorney, Agent, or Firm—Norman Blumenkopf; Murray M. Grill

[57] ABSTRACT

A stabilized enzyme system containing a boron compound, an alpha-hydroxy carboxylic acid, casein and an enzyme is disclosed. The stabilized enzyme system can be used in built liquid aqueous anionic detergent compositions to provide effective proteolytic and amylolytic enzyme cleaning activity to the detergent compositions.

13 Claims, No Drawings

STABILIZED ENZYME SYSTEM FOR USE IN AQUEOUS LIQUID BUILT DETERGENT COMPOSITIONS

CROSS REFERENCE TO RELATED APPLICATION

This application is related to copending U.S. application Ser. No. 792,710 filed on Nov. 30, 1985 which is assigned to a common assignee and which discloses a built aqueous liquid detergent composition containing defined amounts of surfactant builder, and a defined enzyme stabilizing system comprising glycerine, a boron compound, an alpha hydroxy carboxylic acid compound and an enzyme.

This application is also related to copending U.S. application Ser. No. 905,440 filed on Sept. 10, 1986 which is assigned to a common assignee and which discloses an enzyme containing built aqueous liquid detergent composition comprising casein, an enzyme, an anionic surfactant detergent and a polyphosphate builder.

BACKGROUND OF THE INVENTION

This invention relates to built, enzyme-containing liquid detergent compositions suitable for laundry or pre-soak formulations. More particularly, the invention relates to aqueous enzyme-containing liquid detergent compositions which contain one or more detergent builders and which are characterized by being stable compositions.

The formulation of stabilized enzyme-containing liquid detergent compositions has been the focus of much attention in the prior art. The desirability of incorporating enzymes into detergent compositions is primarily due to the effectiveness of proteolytic and amylolytic enzymes in decomposing proteinaceous and starchy materials found on soiled fabrics, thereby facilitating the removal of stains, such as gravy stains, blood stains, chocolate stains and the like during laundering. However, enzymatic materials suitable for laundry compositions, particularly proteolytic enzymes, are relatively expensive. Indeed, they generally are among the most expensive ingredients in a typical commercial liquid detergent composition, even though they are present in relatively minor amounts. Moreover, enzymes are known to be unstable in aqueous compositions, particularly in aqueous built detergent compositions. It is for this reason that an excess of enzymes is generally required in liquid detergent formulations to compensate for the expected loss of enzyme activity during prolonged periods of storage. The prior art is replete with suggestions for stabilizing enzyme-containing powder and liquid detergent compositions, and in particular unbuilt liquid compositions by the use of various materials which are incorporated into the composition to function as enzyme stabilizers.

In the case of liquid detergent compositions containing a phosphate builder, the problem of enzyme instability is particularly acute. This is primarily because phosphate detergent builders have a destabilizing effect on enzymes, even in compositions containing enzyme stabilizers which are otherwise effective in unbuilt formulations. Moreover, the incorporation of a phosphate builder into a liquid detergent composition poses an additional problem, namely the ability to form a stable single-phase composition; the solubility of sodium tripolyphosphate, for example, being relatively limited in aqueous compositions, and especially in the presence of anionic detergents.

Heavy duty aqueous liquid detergents with greater than 5% sodium tripolyphosphate (TPP) are relatively new. The stabilization of enzymes in this type of system is more difficult than with powders containing more than 5% sodium tripolyphosphate (TPP). While it is possible to reduce the pH to improve enzyme stability this negates to some extent the benefit of the builders. The stabilized enzyme system of the present invention provides enzyme stability even at relatively high pH's, up to pH 10–11. The higher pH's, e.g. pH 10–11, are known to give better detergency and are preferred. Reducing the detergent composition pH, e.g. to pH 7.5 to 9.5 can increase the stability of the enzyme, but reduces suds life and the benefits of the builder, i.e. detergency.

PRIOR ART PATENTS

U.S. Pat. No. 3,325,364 discloses a method for the preparation of stabilized aqueous solutions containing a proteolytic enzyme, proteinaceous materials such as gelatin, casein and collagen, and calcium ion for use in aerosol sprays for topical and parenteral application.

U.S. Pat. No. 3,296,094 discloses stabilized aqueous enzyme solutions suitable for use in meat tenderization processes. The dilute aqueous solutions disclosed comprise enzymes, glycerol and partially hydrolyzed and solubilized collagen (protein).

U.S. Pat. No. 3,558,498 discloses a granular detergent composition containing stabilized enzymes, sodium perborate trihydrate, anhydrous trisodium phosphate, anhydrous calcium sulfate and soluble or dispersible proteins having a molecular weight of 5000 to 1,000,000, e.g. casein having a molecular weight of 50,000 to 2000,000.

U.S. Pat. No. 3,560,392 (CINP 3,558,498) discloses a granular detergent composition containing organic detergent, alkaline builder salt, a stabilized enzyme and a stabilizing amount of protenaceous collagen having a molecular weight of 5,000 to 250,000.

U.S. Pat. No. 4,238,345 discloses a liquid proteolytic enzyme containing detergent composition in which the enzyme is stabilized by adding an antioxidant and a hydrophilic polyol having 2 to 6 hydroxyl groups. Patentee states in column 1 that calcium salts combined with proteins and glycerol combined with proteins have been used to provide enzyme stabilizing systems in aqueous liquid detergents.

U.K. Patent Application G.B. No. 2,079,305 discloses an aqueous built enzyme containing liquid detergent composition which is stabilized by a mixture of a polyol and boric acid.

BRIEF DESCRIPTION OF THE INVENTION

In accordance with the present invention there is provided a heavy duty polyphosphate built aqueous liquid detergent composition containing a stabilized enzyme system comprising a boron compound and an alpha-hydroxy carboxylic acid or alpha-hydroxy polycarboxylic acid, and a proteinaceous material, e.g. casein, and an enzyme.

The enzyme stabilization is obtained by premixing a boron and alpha-hydroxy carboxylic acid mixture with an enzyme and casein mixture so as to at the same time block the enzyme catalytic sites with casein and block the enzyme structure with the mixture of the boron compound and the alpha-hydroxy carboxylic acid.

The enzyme stabilizing system of the present invention in addition to providing very good protease stabilization exhibits a very good amylase stabilization, thus allowing the use of dual protease and amylase stabilized systems in high alkaline detergent compositions.

The effective stabilization of amylase enzyme activity is suprising since it would have been expected that any amylase activity would have been destroyed at pH above 9.

In accordance with the present invention, laundering of stained and/or soiled fabrics is affected by contacting the fabrics with a heavy duty built aqueous liquid detergent composition containing the stabilized enzyme system.

The aqueous liquid detergent compositions of the present invention are capable of satisfactorily cleaning laundry items containing both oily and particulate soils. Additionally, the described compositions may be employed for the pretreatment of badly soiled areas, such as collars and cuffs, of items to be laundered.

The present invention is predicated upon the discovery that a stabilizing enzyme system comprising a boron compound, an alpha-hydroxy carboxylic acid or an alpha-hydroxy polycarboxylic acid, a proteinaceous materials, e.g. casein and an enzyme provide an effective and efficient enzyme stabilizing effect to the aqueous liquid detergent compositions of the present invention.

In an embodiment of the present invention there is provided a heavy duty built aqueous liquid detergent composition comprising an enzyme stabilizing system and a suspension of a detergent phosphate builder salt in the aqueous liquid anionic surfactant detergent.

Applicant has found that a stabilizing enzyme system comprising a mixture of a boron compound, an alpha-hydroxy carboxylic acid or an alpha-hydroxy polycarboxylic acid, a proteinaceous material, e.g. casein and an enzyme provided stable, effective enzyme activity over relatively long periods of time.

The detergent formulations of the present invention are stable compositions. The aqueous liquid detergent composition of the present invention are easily pourable, easily measured and easily put into the washing machine.

The aqueous liquid detergent compositions of the present invention can include one or more other detergent builder salts, nonionic and amphoteric surfactants, physical stabilizing agents, viscosity control agents, anti-encrustation agents, pH control agents, optical brighteners, anti-redeposition agents, anti-foam agents, perfumes and dyes.

ADVANTAGES OVER THE PRIOR ART

The present invention provides a heavy duty phosphate built aqueous liquid detergent composition containing a relatively simple stabilized enzyme system which comprises a boron compound, an alpha-hydroxy carboxylic acid or an alpha-hydroxy polycarboxylic acid, a proteineous material, e.g. casein, and an enzyme. The enzyme stabilizing system provides stabilization of the active ingredient enzyme over relatively long periods of time such that smaller amounts of the expensive enzymes can be used.

The present invention provides an aqueous liquid phosphate built anionic surfactant detergent composition that can be used at effective high pH of 10–11.

DETAILED DESCRIPTION OF THE INVENTION

In accordance with the present invention the activity of the enzyme is stabilized over a relatively long period of time such that smaller amounts of the enzyme provide effective enzyme cleaning activity. The enzyme activity is stabilized by the addition of small effective amounts of a stabilized enzyme system comprising a boron compound and an alpha-hydroxy carboxylic acid or an alpha-hydroxy polycarboxylic acid, and a proteinaceous material, e.g. casein and an enzyme. The stabilized enzyme system is used in aqueous phosphate built anionic detergent compositions.

Stabilized Enzyme System

The stabilized enzyme system is preferably prepared separately and then added to the detergent composition.

The stabilized enzyme system is preferably prepared in a three step procedure described as follows.

1. A boron compound is added to an alpha-hydroxy carboxylic acid or salt to obtain a first mixture.
2. The proteinaceous material, e.g. casein is added to an aqueous alkali solution and the enzyme is added to the aqueous alkali solution to obtain a second mixture.
3. The boron and alpha-hydroxy carboxylic acid mixture obtained in step 1 is then mixed with the proteinaceous material and enzyme mixture obtained in step 2 to obtain the stabilized enzyme system of the present invention.

The above step 1 mixture and step 2 mixture can each separately be added to the detergent composition, however, the best enzyme stabilizing results are obtained by premixing the step 1 and step 2 mixtures and then adding the premixed mixture to the detergent composition.

Though applicant does not wish to be limited to any theory of how the stabilized enzyme system operates, it is believed that the boron compound reacts with the alpha-hydroxy carboxylic acid or the alpha-hydroxy polycarboxylic acid to form a boric acid ester. The boric acid ester is believed to react on the enzyme and block its structure in the active conformation so as to protect it from denaturation. The proteinaceous material is believed to block the enzyme catalytic sites hence preventing the digestion of other enzyme molecules during product storage. The stabilized enzyme system comprises:

Boron compound, e.g. Borax, in an amount of 0.5 to 2.5, preferably 0.75 to 2.0 and more preferably 0.9 to 1.2 parts by weight.

Alpha-hydroxy carboxylic acid, in an amount of 1 to 5, preferably 1.5 to 4.0 and more preferably 1.8 to 3.6 parts by weight.

Proteinaceous material, e.g. casein, in an amount of 1 to 6.0, preferably 1 to 4.0, for example 1 to 2.0 parts by weight.

Enzyme in an amount of 0.5 to 3.0, preferably 0.5 to 2.0 and more preferably 0.5 to 1.0 parts by weight.

The weight ratio of alpha-hydroxy carboxylic acid to boron compound, can be 7:1 to 1:1, preferably 4:1 to 1:1, and and more preferably 3:1 to 2:1.

The weight ratio of proteinaceous material, e.g. casein, to enzyme can be 8:1 to 1:1, preferably 4:1 to 1:1 and more preferably 4:1 to 2:1.

A preferred stabilized enzyme system of the present invention comprises the following constituents in the amounts indicated.

|  | Parts by Wt. |
| --- | --- |
| Borax (Na$_2$B$_4$O$_7$.10H$_2$O) | 0.75 to 2.0 |
| Alpha-hydroxy carboxylic acid | 1.5 to 4.0 |
| Casein | 1.0 to 4.0 |
| Enzyme | 0.5 to 2.0 |

The stabilized enzyme system can be added to detergent composition in an amount of 10 to 30 parts of stabilized system to 90 to 70 parts by weight of detergent composition, preferably 15 to 25 parts of stabilized system to 85 to 75 parts by weight of detergent composition and more preferably 15 to 20 parts of stabilized system to 85 to 80 parts by weight of detergent composition.

The stabilized enzyme system of the present invention can be used in aqueous liquid detergent compositions, substantially nonaqueous liquid detergent compositions and in powder or granular detergent compositions. The stabilized enzyme system can be used with anionic surfactants, nonionic surfactants and amphoteric surfactants.

The stabilized enzyme systems of the present invention in a preferred embodiment is added to aqueous liquid anionic phosphate built detergent compositions.

Alpha-Hydroxy Carboxylic Acids

The alpha-hydroxy carboxylic acids that can be used in the present invention are the organic alpha-hydroxy carboxylic acids having 3 to 8 carbon atoms, including 1 to 3 carboxylic acid groups, and 1 to 3 hydroxy groups.

The preferred alpha-hydroxy carboxylic acids are the alpha-hydroxy carboxylic acids having 3 to 6 carbon atoms, including 1 to 3 carboxylic acid groups, and 1 to 2 hydroxy groups. Suitable alpha hydroxy carboxylic acids include malic acid (HOOCCHOHCH$_2$COOH), tartaric acid (HOOCCHOHCHOHCOOH), lactic acid (HOOCCHOHCH$_3$) and citric acid (HOOCCH$_2$COHCOOHCH$_2$COOH). The preferred alpha hydroxy carboxylic acids are tartaric, lactic and citric acids. The citric acid is the most preferred. The acids per se can be used or the acids can be used as their alkali metal salts, such as sodium and potassium salts.

It was found that in some detergent formulations lactic acid tends to induce a phase separation in the suspensions in the detergent compositions. Tartaric acid on the other hand in some detergent formulations tends to enhance the apparent viscosity of the formulation. Citric acid when used in the enzyme stabilizing systems of the present invention was found not to exhibit either of these two problems and is accordingly a preferred alpha-hydroxy carboxylic acid. Citric acid has additional advantages of being readily available and relatively inexpensive.

Boron Compounds

The boron compounds that are used in the present invention are those which are water soluble and when added to water form boric acid or an alkali metal salt of boric acid. The boron compounds that can be used include boric acid, boric oxide or an alkali metal borate. Suitable alkali metal borates are sodium and potassium ortho-, pyro- and meta- borates, polyborates and borax (Na$_2$B$_4$O$_7$.10H$_2$O). The preferred boron compounds are boric acid, sodium borate (Na$_3$BO$_3$) and borax (Na$_2$B$_4$O$_7$.10H$_2$O).

Enzymes

The enzymes to be incorporated in the detergent compositions of the present invention can be proteolytic or amylolytic enzymes or mixtures thereof. The proteolytic enzymes suitable for the present invention include the various commercial liquid, powder or slurry enzymes preparations which have been adapted for use in detergent compositions.

Though the incorporation of the enzyme in the composition is most convenient in liquid form, the enzymes in the slurry form have proven to be useful. Suitable liquid enzyme preparations include "Alcalase" and "Esperase" sold by Novo Industries, Copenhagen, Denmark, "Maxatase" and "Maxacal" sold by Gist-Brocades, Delft, The Netherlands and optimase, sold by Miles Kali Chemie. Suitable proteolytic enzymes include subtilisin, bromelin, papain, trypsin and pepsin. Suitable enzymes include liquid protease and liquid amylase. The enzymes are preferably used as their solutions. A preferred enzyme is Esperase 8L in the form of a solution. Suitable alpha-amylase liquid enzyme preparations are those sold by Novo Industries and Gist-Brocades under the tradenames "Termamyl" and "Maxamyl", respectively. A preferred enzyme is Termamyl 120L. "Esperase" 8L is preferred for the present compositions because of its activity at the higher pH values corresponding to the built detergent compositions. Another preferred enzyme is Esperase 8.0L because of its high activity at 60° C. and its low activity at room temperature. Further, the Esperase 8.0L is stable at high pH, thus allowing a higher pH in the final product and better detergency.

Proteinaceous Material

One of the enzyme stabilizing material constituents of the present invention is a proteinaceous material, for example casein. The proteinaceous materials are used as their water soluble alkali metal salts (e.g. sodium and potassium) and/or are dispersed in an aqueous medium to which the enzyme is added.

Proteins which are soluble or dispersible in water are utilized herein in an effective amount to stabilize the enzymes. Examples of proteins which are soluble or dispersible in water and suitable for use herein include casein (average molecular weight 50,000 to 200,000); Wilsons Protein WSP-X-1000 (a solubilized collagen having an average molecular weight of about 10,000) and Wilson's Hydrolyzate Cosmetic 50, both marketed by Wilson's Pharmaceutical & Chemical Company; and Collagen Hydrolyzate Cosmetic 50, marketed by Maybrook, Inc. A preferred casein protein is sold under the trade name "Sodium Caseinate" by bridal (France) or Dena, A.G. (Germany). The Sodium Caseinate is a mixture of several caseins of different molecular weights. The proteins, e.g. casein, are normally available as powders. The proteins such as casein exist as long chemical chains. As powders the chains are folded upon themselves and form hydrogen bonds holding the protein in a globular form. Unravelling or denaturing the protein involves rupturing these bonds to form a looser more random structure. The proteins can be denatured by boiling, the use of acids, alkalis and various detergents. The unravelled or denatured proteins are more easily digested by enzymes, hence provide a better stabilizing effect, i.e. provide better enzyme stability. The denaturing makes the protein more effective as a stabilizer. The protein, e.g. casein, is used in an amount sufficient to effect stabilization of the enzyme activity.

Surface Active Detergents

The laundry detergent composition may contain one or more surface active agents selected from the group consisting of anionic and nonionic detergents.

The preferred surfactant detergents for use in the present invention are the synthetic anionic detergent compounds and particularly higher alkyl benzene sulfonates, higher alkyl sulfonates and higher alkyl polyether sulfates and mixtures thereof. The anionic detergents may be supplemented, if desired, with nonionic detergents.

Anionic Surfactant Detergents

The anionic surface active agents that are useful in the present invention are those surface active compounds which contain a long chain hydrocarbon hydrophobic group in their molecular structure and a hydrophile group, i.e. water solubilizing group such as sulfonate or sulfate group. The anionic surface active agents include the alkali metal (e.g. sodium and potassium) water soluble higher alkyl benzene sulfonates, alkyl sulfonates, alkyl sulfates and the alkyl poly ether sulfates. The preferred anionic surface active agents are the alkali metal higher alkyl benzene sulfonates and alkali metal higher alkyl polyether sulfates.

The alkyl group in the alkyl benzene sulfonates preferably contain 10 to 16 carbon atoms and more preferably 12 to 15 carbon atoms. Particularly preferred alkyl benzene sulfonates are the sodium or potassium dodecyl and tridecyl benzene sulfonates.

Alkyl sulfonates can be added to the detergent compositions. The alkyl substituent is preferably linear, i.e. normal alkyl, however, branched chain alkyl sulfonates can be employed. The alkyl substituent may be terminally sulfonated or may be joined to the 2-carbon atom of the chain, i.e. may be a secondary sulfonate. The higher alkyl sulfonates can be used as the alkali metal salts, such as sodium and potassium. Alkyl sulfonates such as the $C_{10}$ to $C_{18}$ primary normal alkyl sodium and potassium sulfonates can be used, e.g. the $C_{10}$ to $C_{15}$ primary normal alkyl sodium sulfonate salts.

The higher alkyl polyether sulfates used in accordance with the present invention can be normal or branched chain alkyl and contain lower alkoxy groups which can contain two or three carbon atoms. The normal higher alkyl polyether sulfates are preferred in that they have a higher degree of biodegradability than the branched chain alkyl and the lower poly alkoxy groups are preferably ethoxy groups.

The preferred higher alkyl poly ethoxy sulfates used in accordance with the present invention are represented by the formula $$R^1-O(CH_2CH_2O)_p-SO_3M,$$

wherein $R^1$ is a $C_8$ to $C_{20}$ alkyl, preferably $C_{10}$ to $C_{18}$ and more preferably $C_{12}$ to $C_{15}$; p is 2 to 8, preferably 2 to 6, and more preferably 2 to 4; and M is an alkali metal, such as sodium and potassium, and ammonium cation. The sodium and potassium salts are preferred.

A preferred higher alkyl poly ethoxylated sulfate is the sodium salt of a triethoxy $C_{12}$ to $C_{15}$ alkyl alcohol sulfate having the formula $$C_{12-15}-O-(CH_2CH_2O)_3-SO_3Na.$$

Examples of suitable higher alkyl poly lower alkoxy sulfates that can be used in accordance with the present invention are $C_{12-15}$ normal or primary alkyl triethenoxy sulfate, sodium salt; n-decyl diethenoxy sulfate, sodium salt; $C_{12}$ primary alkyl diethenoxy sulfate, ammonium salt; $C_{15}$ primary alkyl tetraethenoxy sulfate, sodium salt; mixed $C_{14-15}$ normal primary alkyl mixed tri- and tetraethenoxy sulfate, sodium salt; stearyl pentaethenoxy sulfate, sodium salt; and mixed $C_{10-18}$ normal primary alkyl triethenoxy sulfate, potassium salt.

The normal alkyl poly-lower alkoxy sulfates are readily biodegradable and are preferred. The alkyl poly-lower alkoxy sulfates can be used in mixtures with each other and/or in mixtures with the above discussed higher alkyl benzene sulfonates.

The anionic surfactant detergents when used in mixtures of two or more of the detergents can be used in the following amounts.

Alkali metal alkyl benzene sulfonate in an amount of 5 to 20%, preferably 5 to 15% and more preferably 8 to 12%.

Alkali metal alkyl polyether sulfate in an amount of 1 to 20%, preferably 1 to 15% and more preferably 1 to 8%.

Mixtures of alkali metal higher alkyl benzene sulfonates and alkali metal higher alkyl polyether sulfates are preferred.

Alkali metal alkyl sulfonates can optionally be added in an amount of 0 to 20%, such as 1 to 15% and e.g. 5 to 10%.

Nonionic Surfactant Detergent

The nonionic synthetic organic detergents can be used to replace a part of the anionic surfactant detergents.

As is well known, the nonionic synthetic organic detergents are characterized by the presence of an organic hydrophobic group and an organic hydrophilic group and are typically produced by the condensation of an organic aliphatic or alkyl aromatic hydrophobic compound with ethylene oxide (hydrophilic in nature). Typical suitable nonionic surfactants are those disclosed in U.S. Pat. Nos. 4,316,812 and 3,630,929.

Usually, the nonionic detergents are poly-lower alkoxylated lipophiles wherein the desired hydrophile-lipophile balance is obtained from addition of a hydrophilic poly-lower alkoxy group to a lipophilic moiety. A preferred class of the nonionic detergent employed is the poly-lower alkoxylated higher alkanol wherein the alkanol is of 9 to 18 carbon atoms and wherein the number of mols of lower alkylene oxide (of 2 or 3 carbon atoms) is from 3 to 12. Of such materials it is preferred to employ those wherein the higher alkanol is a higher fatty alcohol of 9 to 11 or 12 to 15 carbon atoms and which contain from 5 to 8 or 5 to 9 lower alkoxy groups per mol.

Exemplary of such compounds are those wherein the alkanol is of 12 to 15 carbon atoms and which contain about 7 ethylene oxide groups per mol, e.g. Neodol 25-7 and Neodol 23-6.5, which products are made by Shell Chemical Company, Inc. The former is a condensation product of a mixture of higher fatty alcohols averaging about 12 to 15 carbon atoms, with about 7 mols of ethylene oxide and the latter is a corresponding mixture wherein the carbon atom content of the higher fatty alcohol is 12 to 13 and the number of ethylene oxide groups present averages about 6.5. The higher alcohols are primary alkanols.

Other useful nonionics are represented by the commercially well known class of nonionics sold under the trademark Plurafac. The Plurafacs are the reaction product of a higher linear alcohol and a mixture of ethylene and propylene oxides, containing a mixed chain of ethylene oxide and propylene oxide, terminated by a hydroxyl group. Examples include Product A (a $C_{13}$–$C_{15}$ fatty alcohol condensed with 6 moles ethylene oxide and 3 moles propylene oxide), Product B (a $C_{13}$–$C_{15}$ fatty alcohol condensed with 7 moles propylene oxide and 4 moles ethylene oxide), Product C (a $C_{13}$–$C_{15}$ fatty alcohol condensed with 5 moles propylene oxide and 10 moles ethylene oxide), and Product D (a mixture of equal parts Product C and Product B).

Another group of liquid nonionics are commercially available from Shell Chemical Company, Inc. under the Dobanol trademark: Dobanol 91-5 is an ethoxylated $C_9$–$C_{11}$ fatty alcohol with an average of 5 moles ethylene oxide and Dobanol 25-7 is an ethoxylated $C_{12}$–$C_{15}$ fatty alcohol with an average of 7 moles ethylene oxide per mole of fatty alcohol.

In the compositions of this invention, preferred nonionic surfactants include the $C_{12}$–$C_{15}$ secondary fatty alcohols with relatively narrow contents of ethylene oxide in the range of from about 7 to 9 moles, and the C9 to C11 fatty alcohols ethoxylated with about 5–6 moles ethylene oxide.

Mixtures of two or more of the liquid nonionic surfactants can be used.

BUILDER SALTS

The liquid aqueous anionic or anionic and nonionic surfactant compositions used in the present invention has dispersed and suspended therein particles of inorganic and/or organic detergent builder salts.

The invention detergent compositions include water soluble and/or water insoluble detergent builder salts. Water soluble inorganic alkaline builder salts which can be used alone with the detergent compound or in admixture with other builders are alkali metal carbonates, bicarbonates, phosphates, polyphosphates, and silicates. (Ammonium or substituted ammonium salts can also be used.) Specific examples of such salts are sodium tripolyphosphate, sodium carbonate, sodium pyrophosphate, potassium pyrophosphate, sodium bicarbonate, potassium tripolyphosphate, sodium hexametaphosphate, sodium sesquicarbonate, sodium mono and diorthophosphate, and potassium bicarbonate. Sodium tripolyphosphate (TPP) and sodium hexametaphosphate are preferred.

The polyphosphate builder (such as sodium tripolyphosphate) can be supplemented with suitable organic auxiliary builders.

Suitable organic builders are polymers and copolymers of polyacrylic acid and polymaleic anhydride and the alkali metal salts thereof. More specifically such builder salts can consist of a copolymer which is the reaction product of about equal moles of methacrylic acid and maleic anhydride which has been partially or completely neutralized to form the sodium salt thereof. The partially neutralized builder is available under the trade name Sokalan CP45 and the completely neutralized builder is available under the tradename Sokalan CP5. These builders serve when used even in small amounts to inhibit incrustation.

Examples of organic alkaline sequestrant builder salts which can be used with the detergent builder salts or in admixture with other organic and inorganic builders are alkali metal, ammonium or substituted ammonium, aminopolycarboxylates, e.g. sodium and potassium ethylene diaminetetraacetate (EDTA), sodium and potassium nitrilotriacetates (NTA), and triethanolammonium N-(2-hydroxyethyl)nitrilodiacetates. Mixed salts of these aminopolycarboxylates are also suitable.

Other suitable builders of the organic type include carboxymethylsuccinates, tartronates and gylcollates. Of special value are the polyacetal carboxylates. The polyacetal carboxylates and their use in detergent compositions are described in U.S. Pat. Nos. 4,144,226, 4,315,092 and 4,146,495.

The inorganic alkali metal silicates are useful builder salts which also function to adjust or control the pH and to make the composition anticorrosive to washing machine parts. Sodium silicates of $Na_2O/SiO_2$ ratios of from 1.6/1 to 1/3.2, especially about ½ to ⅛.8 are preferred. Potassium silicates of the same ratios can also be used.

The water insoluble crystalline and amorphous aluminosilicate zeolite detergent builder salts can be used. The zeolites generally have the formula

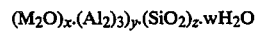

$$(M_2O)_x \cdot (Al_2)_3)_y \cdot (SiO_2)_z \cdot wH_2O$$

wherein x is 1, y is from 0.8 to 1.2 and preferably 1, z is from 1.5 to 3.5 or higher and preferably 2 to 3 and w is from 0 to 9, preferably 2.5 to 6 and M is preferably sodium. A typical zeolite is type A or similar structure, with type 4A particularly preferred. The preferred aluminosilicates have calcium ion exchange capacities of about 200 miliequivalents per gram or greater, e.g. 400 meq 1g.

Various crystalline zeolites (i.e. alumino-silicates) that can be used are described in British Pat. No. 1,504,168, U.S. Pat. No. 4,409,136 and Canadian Pat. Nos. 1,072,835 and 1,087,477, all of which are hereby incorporated by reference for such descriptions. An example of amorphous zeolites useful herein can be found in Belgium Patent 835,351 and this patent too is incorporated herein by reference.

Other materials such as clays, particularly of the water-insoluble types, may be useful adjuncts in compositions of this invention. Particularly useful is bentonite. This material is primarily montmorillonite which is a hydrated aluminum silicate in which about 1/6th of the aluminum atoms may be replaced by magnesium atoms and with which varying amounts of hydrogen, sodium, potassium, calcium, etc., may be loosely combined. The bentonite in its more purified form (i.e. free from any grit, sand, etc.) suitable for detergents contains at least 50% montmorillonite and thus its cation exchange capacity is at least about 50 to 75 meq per 100 g of bentonite.

The bentonite employed herein is a colloidal clay. Swelling bentonites are generally characterized as sodium bentonites, i.e. bentonite wherein the predominant cation is sodium. Among the sodium bentonite clays, those from Wyoming (generally referred to as Western or Wyoming bentonite) are preferred.

The swelling capacity of bentonite is generally associated with its fabric softening properties. The softening properties of bentonites are described in British Patent 401,413 to Marriott and British Patent 461,221 to Marriott and Guan. In water, the swelling capacity of sodium bentonite is in the range of 3 to 20 milliliters/gram, preferably 7 to 15 ml/gram, and its viscosity, at 6% concentration in water, is usually in the range of 3 to 30 centipoises, preferably 8 to 30 centipoises.

Preferred swelling bentonites are sold under the trademark HI-JEL by Georgia Kaolin Co. These materials are the same as bentonites which were formerly sold under the trademarks MINERAL COLLOID and THIXO-JEL. They are selectively mined and beneficated bentonites, and those considered to be most useful are available as HI-JEL Nos. 1,2,3 and 4, corresponding to THIXO-JELs Nos. 1,2,3 and 4. Such materials have a maximum free moisture content (before addition to the liquid medium) of 4% to 8% and specific gravities of about 2.6. The bentonite is preferably one which will pass through a 200 mesh U.S. Sieve Series sieve, and most preferably at least 90% of the particles will pass through a No. 325 sieve, so that the equivalent diameter of the bentonite may be considered to be less than 74 microns, and more preferably less than about 44 microns.

Although the western bentonites are preferred it is also possible to utilize other bentonites, such as those which may be made by treating Italian or similar bentonites containing relatively small proportions of exchangeable monovalent metals (sodium and potassium) with alkaline materials, such as sodium carbonate, to increase the cation exchange capacities of such products. It is considered that the $Na_2O$ content of the bentonite should be at least about 0.5%, preferably at least 1% and more preferably at least 2% so that the clay will be satisfactorily swelling, with good softening and dispersing properties in aqueous suspension. Preferred swelling bentonites of the types described above are sold under the tradenames Laviosa and Winkelmann, e.g. Laviosa AGB and Winkelmann G-13.

Other bentonites which are particularly useful for the present liquid detergent compositions because of their white or very light color include American Colloid Company's Polarite KB 325, a California bentonite, and Georgia Kaolin's GK 129, a Mexican bentonite.

In addition to the detergent builders, various other detergent additives or adjuvants may be present in the detergent product to give it additional desired properties, either of functional or aesthetic nature.

Thus, improvements in the physical stability and anti-settling properties of the composition may be achieved by the addition of a small effective amount of an aluminum salt of a higher fatty acid, e.g. aluminum stearate, to the composition. The aluminum salt stabilizing agents are the subject matter of the commonly assigned copending application Ser. No. 725,455 filed Apr. 22, 1985, the disclosure which is incorporate herein by reference thereto. The aluminum stearate stabilizing agent can be added in an amount of 0 to 3%, preferably 0.1 to 1.0% and more preferably 0.1 to 0.5%. The aluminum stearate besides its stabilizing effect also improves the product dispensibility in the washing machine.

There also may be included in the formulation, minor amounts of soil suspending or anti-redeposition agents, e.g. polyvinyl alcohol, fatty amides, sodium carboxymethyl cellulose and sodium, hydroxy-propyl methyl cellulose. Preferred anti-redeposition agents are sodium carboxymethyl cellulose having a 2:1 ratio of CM/MC which is sold under the tradename Relatin DM 4050, and sodium methyl hydroxypropyl cellulose.

Optical brighteners for cotton, polyamide and polyester fabrics can be used. Suitable optical brighteners include Tinopal LMS-X, stilbene, triazole and benzidine sulfone compositions, especially sulfonated substituted triazinyl stilbene, sulfonated naphthotriazole stilbene, benzidene sulfone, etc., most preferred are stilbene and triazole combinations. A preferred brightener is Tinopal LMS-X. Another preferred optical brightener is Stilbene Brightener N4 which is a dimorpholine dianilino stilbene sulfonate.

Anti-foam agents, e.g. silicon compounds, such as Silicone DB100, can also be added in small effective amounts, e.g. 1% by weight (100% A.I.).

Bactericides, e.g. tetrachlorosalicylanilide and hexachlorophene, fungicides, dyes, pigments (water dispersible), preservatives, e.g. formalin, ultraviolet absorbers, anti-yellowing agents, such as sodium carboxymethyl cellulose, pH modifiers and pH buffers, perfume, and dyes and bluing agents such as Iragon Blue L2D, Detergent Blue 472/572 and ultramarine blue can be used. A preferred bactericide is Oxaban A, from Angus Chemie (Germany) and a preferred dye is Acilan blue.

The viscosity of the present aqueous clay softergent composition can be in range of 1000 to 2500 centipoises, preferably 1500 to 2000 centipoises, but products of other suitable viscosities can also be useful. At the viscosities mentioned, the liquid detergent forms a stable composition and is easily pourable. The pH of the liquid detergent composition can be in the range of 7.0 to 12, preferably 8.6 to 11.5 and more preferably 9.0 to 11.0.

In the heavy duty aqueous liquid detergent composition of the present invention, typical proportions (percent based on the total weight of composition, unless otherwise specified) of the ingredients are as follows:

Water in an amount of 30 to 60%, preferably 35 to 55% and more preferably 45 to 55% by weight.

Phosphate detergent builder, such as sodium tripolyphosphate (TPP) and sodium hexametaphosphate, in an amount of 5 to 30%, preferably 8 to 25% and more preferably 8 to 20% by weight.

Clay fabric softening agent in an amount of 0 to 15%, preferably 5 to 15% and more preferably 8 to 15% by weight.

Liquid anionic surfactant detergent in an amount of 5 to 40%, preferably 10 to 25% and more preferably 10 to 15% by weight.

Liquid nonionic surfactant detergent in an amount of 0 to 20%, preferably 0.5 to 10% and more preferably 1 to 5% by weight.

Alkali metal carbonate in an amount of 1 to 15%, preferably 1 to 8% and more preferably 1 to 4% by weight.

Anti-redeposition agent, such as alkali metal carboxymethyl cellulose and alkali metal methyl hydroxypropyl cellulose, in an amount of 0 to 3.0%, preferably 0.1 to 2%, e.g. 0.1 to 1%.

Alkali metal silicate in an amount of 0 to 15%, preferably 0.5 to 10% and more preferably 1 to 5% by weight.

Boron compound, e.g. borax ($Na_2B_4O_7 \cdot 10H_2O$), in an amount of 0.5 to 2.5%, such as 0.7 to 2.2%, for example 0.75 to 2.0% and 0.9 to 1.2% by weight.

Alpha-hydroxy carboxylic acid and alpha-hydroxy polycarboxylic acid, in an amount of 1 to 5.0%, preferably 1.5 to 4.0% and more preferably 1.8 to qb 3.6%.

Proteinaceous material, e.g. casein, in an amount of 1.0 to 6%, preferably 1.0 to 4% and more preferably 1.0 to 2.0%.

Enzyme in an amount of 0.5 to 3%, preferably 0.5 to 2% and more preferably 0.5 to 1.0%.

Physical stabilizing agent, e.g. aluminium stearate in an amount of 0 to 3%, preferably 0.1 to 2.0%, and more preferably 0.1 to 5% by weight.

Anti-foam agent in an amount of 0 to 8%, preferably 0.5 to 6.0% and more preferably 0.5 to 1.5%.

Preservative, e.g. Oxaban A in an amount of 0 to 1.0%, preferably 0.1 to 0.5%, for example 0.1 to 0.4%.

Optical brightener in an amount of 0.1 to 1.0%, preferably 0.25 to 1.0%, e.g. 0.30 to 1.0% by weight.

Dye in an amount of 0 to 0.1%, preferably 0.1 to 0.1%, e.g. 0.02 to 0.08%.

Perfume in an amount of 0 to 3.0%, preferably 0.25 to 0.25%, e.g. 0.30 to 1.0%.

Various of the previously mentioned other conventional additives can optionally be added to achieve the desired function of the added materials.

In the selection of the additives, they will be chosen to be compatible with the enzyme stabilizing function of the protein, e.g. casein and the main active constituents of the detergent composition. In this application, as mentioned above, all percentages are by weight of the entire formulation or composition unless otherwise indicated.

The heavy duty aqueous liquid detergent compositions of the present invention dispense readily in the water in the washing machine.

In a preferred embodiment of the invention the detergent composition of a typical formulation using the following named ingredients.

DETERGENT COMPOSITION FORMULATION

In a preferred embodiment of the invention a detergent composition of a typical formulation containing the stabilizing enzyme system of the present invention is formulated using the following named ingredients:

|  | Weight % |
|---|---|
| Water | 40–55 |
| Phosphate Builder Salt | 5–30 |
| Anionic Surfactant Detergent: | |
| Linear alkyl benzene sulfonate[1] | 5–20 |
| Linear alkyl ether sulfate[2] | 1–8 |
| Sodium Carbonate | 1–4 |
| Sodium Carboxymethyl Cellulose | 0.1–1 |
| Boron Compound | 0.8 to 2.2 |
| Alpha Hydroxy Carboxylic Acid | 1.8 to 3.6 |
| Casein | 1.0 to 4.0 |
| Enzyme | 0.5 to 2.0 |
| Physical Stabilizing Agent[3] | 0.1 to 0.5 |
| Optical Brightener | 0.25 to 1.0 |
| Anti-foam Agent | 0 to 8 |
| Dye | 0 to 0.10 |
| Perfume | 0 to 1.0 |

[1]A suitable linear alkyl benzene sulfonate is sodium dodecyl or tridecyl benzene sulfonate.
[2]A suitable linear alkyl ether sulfate is Empinin KSN70, which is sodium lauryl ether (3EO) sulfate sold by Albright and Wilson.
[3]A suitable physical stabilizing agent is aluminium stearate.
[4]A particularly efficient anti-foam agent is Silicone DB100 (100% A.I.) from DOW Corning which can be used in amounts of for example 0.5 to 2%, such as about 1%.

SOFTERGENT COMPOSITION FORMULATION

|  | Weight % |
|---|---|
| Water | 45–55 |
| Sodium Hexametaphosphate[1] | 5–15 |
| Clay Softener[2] | 5–15 |
| Anionic Surfactant: | |
| Linear Alkyl Benzene Sulfonate[3] | 5–15 |
| Linear Alkyl Ether Sulfate[4] | 1–10 |
| Sodium Carbonate | 1–6 |
| Sodium Carboxymethyl Cellulose | 0.1–1.0 |
| Boron Compound | 0.5–2.2 |
| Alpha Hydroxy Carboxylic Acid | 1.5–4.0 |
| Casein | 1–4 |
| Enzyme | 0.5–2.0 |
| Physical Stabilizing Agent[5] | 0.1–0.5 |
| Optical Brightener | 0.25 to 1.0 |
| Anti-foam Agent (10% solution) | 0–8.0 |
| Dye | 0.02 to 0.10 |
| Perfume | 0 to 1.0 |

[1]The sodium hexametaphosphate is Hexa 25, marketed by CPA (Brussels).
[2]The clay softener agent is Bentonite G13 marketed by Winkelman (Italy).
[3]Sodium dodecyl benzene sulfonate.
[4]Sodium linear lauryl ether sulfate (Empinin KSN70).
[5]Aluminium stearate.

The present invention is further illustrated by the following examples.

EXAMPLE 1

A proteolytic enzyme, i.e. Esperase, is stabilized in accordance with the present invention by the preparation of an enzyme stabilizing system using the following procedure.

(1) One hundred thirteen grams of Borox ($Na_2B_4O_7 \cdot 10H_2O$) are added with stirring to 253 gms of lactic acid at room temperature. The boron and lactic acid mixture is neutralized with about 115 gms of 23 N NaOH to about pH 7.

(2) Twenty grams of casein, marketed by Bridel, are added to 80 gms of 0.17N NaOH solution with stirring and heating to 50° C. to dissolve or disperse the casein. Ten gm of Esperase 8L enzyme, marketed by Novo, is added with stirring to disperse the enzyme in the casein solution or dispersion. The casein and Esperase mixture is cooled to room temperature.

In order to obtain the enzyme stabilized system of the present invention, 24 gms of the boron lactic acid mixture obtained in step 1 above is added to about 33 gms of the enzyme and casein mixture obtained in the above step 2 and the medium brought to pH 9.5 by addition of a 23N solution of NaOH.

A stabilized enzyme system containing the following ingredients in the amounts indicated was obtained.

|  | Parts by Weight |
|---|---|
| $Na_2B_4O_7 \cdot 10H_2O$ | 0.9 |
| Lactic Acid | 2.1 |
| Casein | 1.0 |
| Esperase 8L | 0.5 |

The above stabilized enzyme system can be added to a detergent or softergent composition to provide enzyme cleaning function.

EXAMPLE 2

A stabilized enzyme system was prepared in accordance with the present invention containing the following ingredients.

|  | Parts by Weight |
|---|---|
| $Na_2B_4O_7 \cdot 10H_2O$ | 0.9 |
| Lactic Acid | 1.8 |
| Casein | 2.0 |
| Esperase 8.0L | 0.5 |
| Termamyl 120L | 0.3 |

About 15 parts by weight of the stabilized enzyme system was added to about 85 parts by weight of a softergent composition with the necessary adjustments made to the composition to obtain concentrations of the stabilized enzyme system ingredients in percent by weight of the entire composition equal to the parts by weight of the ingredients in the stabilized system.

The resulting softergent composition contained the following ingredients in the indicated amounts.

|  | Wt. % |
|---|---|
| Water | 54.8 |
| Sodium Tripolyphosphate | 11.0 |
| Clay Softener | 9.0 |
| LAS[1] | 10.1 |
| LES[2] | 2.2 |
| Sodium Carbonate | 2.0 |
| Sodium Carboxymethyl Cellulose | 0.2 |
| Sodium Methylhydroxypropyl Cellulose | 0.2 |
| Borax ($Na_2B_4O_7.10H_2O$) | 0.9 |
| Lactic Acid | 1.8 |
| Casein | 2.0 |
| Esperase 8L | 0.5 |
| Termamyl 120L | 0.3 |
| SP 3 Anti-foam Agent[3] (10% A.I.) | 4.0 |
| Laponite RDS[4] | 0.8 |
| Aluminium Stearate[5] | 0.2 |
|  | 100.0 |

[1]LAS is sodium linear dodecyl benzene sulfonate.
[2]LES is sodium $C_{12}$ linear alkyl (3 ethoxy) sulfate.
[3]SP3 Anti-foam agent is silcone powder, marketed by Wacker.
[4]Laponite RDS is synthetic montmorillonite.
[5]Aluminium stearate is a physical stabilizing agent and improves the physical stability of the softergent composition.

The softergent composition containing both Esperase 8L and Termamyl 120L enzymes was tested for Proteolytic enzyme activity after ageing at room temperature, 35° C. and 43° C. for 1, 4 and 8 weeks. Comparative tests were made at the same time with the commercial products "New Vizir", and "Wisk" which contains a glycerine-Borox enzyme stabilizing system. The results obtained are reported in the following Table 1.

TABLE 1

| Ageing Temperature | Proteolytic Activity | | | | | | | | |
|---|---|---|---|---|---|---|---|---|---|
|  | Room Temp | | | 35° C. | | | 43° C. | | |
| Ageing Time (Wks) | 1 | 4 | 8 | 1 | 4 | 8 | 1 | 4 | 8 |
| Invention (pH 10.6) | 95 | 85 | 100 | 75 | 56 | 60 | 32 | 22 | 21 |
| New Vizir (pH 7.5) | 100 | 96 | 91 | 66 | 42 | 20 | 16 | 19 | 19 |
| Wisk (pH 7.4) | 99 | 92 | 79 | 87 | 50 | 30 | 44 | 17 | 5 |

The Table 1 data show that the Proteolytic activity of the invention stabilized enzyme system, even though at a higher pH 10.6 was better than that of the commercial products New Vizir and Wisk after ageing for 1,4 and 8 weeks. The good Proteolytic activity of the stabilized enzyme system of the present invention was obtained at pH 10.6 as compared to the New Vizir at pH 7.5 and the Wisk at pH 7.4, which means that the detergency properties of the invention composition would be expected to be superior because of the higher pH 10.6.

EXAMPLE 3

The softergent composition of Example 2 containing the stabilized enzyme system of the present invention comprising both Esperase 8L and Termamyl 120L enzymes was then tested for Amylolytic enzyme activity after aging at room temperature, 35° C. and 43° C. for 1, 4 and 8 weeks. Comparative tests were made at the same time with the commercial product "New Vizir". The results obtained are reported in the following Table 2.

TABLE 2

| Ageing Temperature | Amylolytic Activity | | | | | | | | |
|---|---|---|---|---|---|---|---|---|---|
|  | Room Temp | | | 35° C. | | | 43° C. | | |
| Ageing Time (Wks) | 1 | 4 | 8 | 1 | 4 | 8 | 1 | 4 | 8 |
| Invention (pH 10.6) | 100 | 100 | 100 | 99 | 94 | 89 | 83 | — | 17 |
| New Vizir (pH 7.5) | — | 99 | 95 | — | 97 | 80 | — | 61 | 4 |

The Table 2 data show that the Amylolytic activity of the stabilized enzyme system, even though at a higher pH 10.6 was at least as good as or slightly better than the New Vizir after ageing at room temperature, 35° and 43° C. for 1, 4 and 8 weeks. The good Amylolytic activity of the stabilized enzyme system of the present invention was obtained at pH 10.6 as compared to the New Vizar pH 7.5, which means that the detergency properties of the invention composition would be expected to be superior because of the higher pH 10.6.

EXAMPLE 4

A stabilized enzyme system was prepared in accordance with the present invention as follows:

1. 340 gms of lactic acid (85% conc.) were added to 150 gms of Borax ($Na_2B_4O_7.10H_2O$) and mixed with 80 gms of water containing 74 gms of NaOH.

2. 12 gms of casein was mixed with 48 gms of water containing 0.4 gm of NaOH at 50° C. after which there was added 6.0 gms of Esperase 8L.

3. 48 gms of the lactic acid and boron mixture of step 1 was mixed with the casein and Esperase 8L mixture of step 2 and a concentrated NaOH solution was added to obtain about 120 gms of mixture of about pH 9.

About one hundred and twenty grams of the stabilized enzyme system were added to about 480 gms of a softergent composition to obtain the following composition.

|  | Wt. % |
|---|---|
| Water | 52.5 |
| Sodium Hexametaphosphate[1] | 10.0 |
| Clay[2] | 10.0 |
| LAS[3] | 9.2 |
| Empimin KSN70[4] | 3.2 |
| Sodium Carbonate | 1.0 |
| Sodium Carboxymethyl Cellulose | 0.1 |
| Sodium Methylhydroxy Propyl Cellulose | 0.2 |
| Borax ($Na_2B_4O_7.10H_2O$) | 1.9 |
| Lactic Acid | 3.6 |
| Casein | 2.0 |
| Esperase 8L | 1.0 |
| SP 3 Anti-foam Agent[5] (10% A.I.) | 4.0 |
| Laponite RDS[6] | 0.5 |
| Dynadet[7] | 0.3 |
| Aluminium Stearate[8] | 0.2 |
| Tenopal CMS-X[9] | 0.3 |
|  | 100.0 |

The softergent composition as prepared has a pH 9.1.
[1]Sodium Hexametaphosphate is Hexa 25 and which is supplied by C.P.A. Brussels.
[2]Thioxogel No. 1 is sodium bentonite and is supplied by American Colloid.
[3]LAS which is sodium dodecyl benzene sulfonate.
[4]Empimin KSN70 is sodium linear lauryl ethoxy (3EO) sulfate and is supplied by Albright and Wilson.
[5]SP3 is a silicone compound and is supplied by Wacker Chemie (Germany).
[6]Laponite RDS is synthetic montmorillonite and is supplied by Laporte Industries, Ltd.
[7]Dynadet plus is a perfume and is supplied by IFF (The Netherlands).
[8]Aluminium stearate is a physical stabilizing agent for the softergent composition.
[9]Tinopal CMS-X is a commercially available optical brightener.

EXAMPLE 5

A stabilized enzyme system premix is prepared in accordance with the present invention containing the following ingredients.

|  | Parts by Wt. |
|---|---|
| $Na_2B_4O_7 \cdot 10H_2O$ | 0.9 |
| Citric Acid | 2.6 |
| Casein | 2.0 |
| Esperase 8.0L | 0.5 |
| Termamyl 120L | 0.3 |

A heavy duty aqueous liquid laundry detergent composition is prepared by adding about 20 parts by weight of stabilized enzyme system to about 80 parts by weight of a detergent composition to obtain a detergent composition containing the following ingredients in the amounts specified.

|  | Wt. % |
|---|---|
| Water | 53.48 |
| Sodium Tripolyphosphate (TPP) | 15.0 |
| Sodium Linear Tridecylbenzene Sulfonate | 14.3 |
| Sodium Linear Lauryl Ethoxylated (3EO) Sulfate | 5.0 |
| Sodium Carbonate | 4.0 |
| Sodium Carboxy Methyl Cellulose | 0.2 |
| $Na_2B_4O_7 \cdot 10H_2O$ | 0.8 |
| Citric Acid | 2.6 |
| Casein[1] | 2.0 |
| Esperase 8.0L[2] | 0.5 |
| Termamyl 120L[3] | 0.3 |
| Anti-foam Agent[4] | 1.0 |
| Aluminium Stearate[5] | 0.1 |
| Optical Brightener | 0.4 |
| Blue Dye | 0.02 |
| Perfume | 0.3 |
|  | 100.00 |

[1]Casein marketed by Bridel.
[2]Esperase 8.0L is marketed by Novo.
[3]Termamyl 120L is marketed by Novo.
[4]Anti-foam DB 100, marketed by Dow Corning.
[5]Aluminium stearate is a physical stabilizing agent and maintains the physical stability of the composition.

The proceeding composition can be prepared by the following procedure: 24.0 parts of water at 40° F. are added to a suitable mixing apparatus equipped with a stirrer. A mixture consisting of 4.0 parts sodium carbonate and 0.2 parts sodium carboxy methyl cellulose is added to the water with stirring. 15.0 parts of sodium tripolyphosphate is slowly added to the mixture with further stirring to form a suspension.

Thereafter 20.7 parts of the enzyme premix, containing 0.8 parts Borax, 2.6 parts citric acid, 2.0 parts casein, 0.5 parts Esperase 8L and 0.3 parts Termamyl 120L are added with continued stirring. Afterwards 17.8 parts of a premix containing NaLAS (9.13 parts), DB100 (1.0 part) and aluminum stearate (0.1 part) are added with stirring and dispersed; and 0.4 part optical brightener, 0.02 part blue dye and 0.3 part perfume are edded with continued stirring. Finally 17.7 parts of a premix constituted of NaLAS (5.17 parts) and linear ethoxylated sulfate (5.0 parts) are added to form the aqueous detergent composition.

The water content of the mixture is adjusted to obtain the weight percent of the specified ingredients as shown above.

In the above formulating procedure the ingredients and the proportions thereof can be varied by those skilled in the art to obtain desired detergent compositions of specific detergent ingredients and proportions.

It is understood that the foregoing detailed description is given merely by way of illustration and that variations may be made therein without departing from the spirit of the invention.

What is claimed is:

1. A heavy duty built aqueous liquid detergent composition containing a stabilized enzyme system wherein said detergent composition comprises

|  | Weight [by] % |
|---|---|
| Water | 30–60 |
| Phosphate Builder Salt | 5–30 |
| Anionic Surfactant or mixture of anionic and nonionic surfactant | 10–25 |
| Clay Softener | 0–15 |
| and said stabilized enzyme system comprises |  |
| Boron Compound | 0.5 to 2.5 |
| Alpha-hydroxy Carboxylic Acid | 1 to 5 |
| [Proteinaceous Material] Casein | 1 to 6 |
| Enzyme | 0.5 to 3 |

2. The heavy duty built aqueous liquid detergent composition of claim 1 comprising 5 to 15% by weight of clay softener.

3. The heavy duty built aqueous liquid detergent composition of claim 1 wherein said boron compound is at least one of borax ($Na_2B_4O_7 \cdot 10H_2O$), sodium borate ($Na_3BO_3$), boric acid and boric oxide.

4. A heavy duty built aqueous liquid detergent composition containing a stabilized enzyme system wherein said detergent composition comprises

|  | Weight % |
|---|---|
| Water | 45–55 |
| Sodium Tripolyphosphate (TPP) | 5–30 |
| Anionic Surfactant Detergent: |  |
| Linear Alkyl Benzene Sulfonate | 5–15 |
| Linear Alkyl Ethoxy Sulfate | 1–8 |
| Sodium Carbonate | 1–8 |
| Sodium Carboxymethyl Cellulose | 0.1 to 1 | and said stabilized enzyme system consisting essentially of

|  | Weight % |
|---|---|
| Borax ($Na_2B_4O_7 \cdot 10H_2O$) | 0.75 to 2.0 |
| Alpha Hydroxy Carboxylic Acid | 1.5 to 4.0 |
| Casein | 1.0 to 4.0 |
| Enzyme | 0.5 to 2.0 |

5. The heavy duty built aqueous liquid detergent composition of claim 4 wherein the linear alkyl benzene sulfonate is sodium linear tridecylbenzene sulfonate and the linear alkyl ethoxy sulfate is lauryl ether sulfate (three ethoxy) sodium sulfate.

6. The heavy duty built aqueous liquid detergent composition of claim 4 wherein the alpha hydroxy carboxylic acid is at least one of lactic acid, tartaric acid, citric acid and the sodium salts thereof.

7. The heavy duty built aqueous liquid detergent composition of claim 1 wherein the alpha-hydroxy carboxylic acid comprises citric acid and the sodium salt thereof.

8. A heavy duty built aqueous liquid detergent composition containing a stabilized enzyme system wherein said detergent composition comprises

|  | Weight % |
|---|---|
| Water | 40–55 |
| Sodium Hexametaphosphate | 5–15 |
| Clay Softener | 5–15 |

-continued

| Anionic Surfactant | Weight % |
| --- | --- |
| Linear Alkyl Benzene Sulfonate | 5-15 |
| Linear Ethoxylated Sulfate | 1-10 |
| Sodium Carbonate | 1-8 |
| Sodium Carboxymethyl Cellulose | .1 to 1.0 | and said stabilized enzyme system comprises

| | Weight % |
| --- | --- |
| Borax (Na$_2$Ba$_4$O$_7$.10H$_2$O) | 0.75 to 2.0 |
| Alpha Hydroxy Carboxylic Acid | 1.5 to 4.0 |
| Casein | 1.0 to 4.0 |
| Enzyme | 0.5 to 2.0 |

9. The heavy duty built aqueous liquid detergent composition of claim 8 wherein the linear alkyl benzene sulfonate is sodium linear dodecyl benzene sulfonate and the linear ethoxylate sulfate is linear $C_{12}$ to $C_{15}$ alkyl (three ethoxy) sodium sulfate.

10. The heavy duty built aqueous liquid detergent composition of claim 8 wherein the alpha hydroxy carboxylic acid is at least one of lactic acid, tartaric acid, citric acid and the sodium salts thereof.

11. A method for cleaning soiled fabrics which comprises adding to an aqueous wash liquor the built aqueous liquid detergent composition of claim 1 in a sufficient amount to clean soiled fabrics.

12. A method for cleaning soiled fabrics which comprises adding to an aqueous wash liquor the built aqueous liquid detergent composition of claim 3 in a sufficient amount to clean soiled fabrics.

13. A method for cleaning soiled fabrics which comprises adding to an aqueous wash liquor the built aqueous liquid detergent composition of claim 4 in a sufficient amount to clean soiled fabrics.

* * * * *